(12) United States Patent
Chan

(10) Patent No.: US 6,663,605 B2
(45) Date of Patent: Dec. 16, 2003

(54) REMOVABLE PROTECTIVE CANNULA FOR USE IN SURGERY

(76) Inventor: Kwan-Ho Chan, 4803 1st Place, Lubbock, TX (US) 79416

( * ) Notice: Subject to any disclaimer, the term of this patent is extended or adjusted under 35 U.S.C. 154(b) by 44 days.

(21) Appl. No.: 09/728,140

(22) Filed: Dec. 1, 2000

(65) Prior Publication Data

US 2002/0068911 A1 Jun. 6, 2002

Related U.S. Application Data

(60) Provisional application No. 60/168,591, filed on Dec. 2, 1999.

(51) Int. Cl.[7] .............................................. A61M 5/00
(52) U.S. Cl. ....................................... 604/263; 604/192
(58) Field of Search ................................. 604/168, 164, 604/264; 606/198

(56) References Cited

U.S. PATENT DOCUMENTS 4,280,508 A * 7/1981 Barrada .................. 128/736 Q
5,674,240 A * 10/1997 Bonutti et al. ............. 606/198

* cited by examiner

*Primary Examiner*—Henry Bennett
*Assistant Examiner*—Sabrina Dagostino
(74) *Attorney, Agent, or Firm*—Pandiscio & Pandiscio, PC

(57) ABSTRACT

A removable protective cannula is disclosed for use in surgery to prevent damage to a portal cannula or tissue during insertion of a shaft instrument.

10 Claims, 5 Drawing Sheets

Side View of Removable Protective Cannula

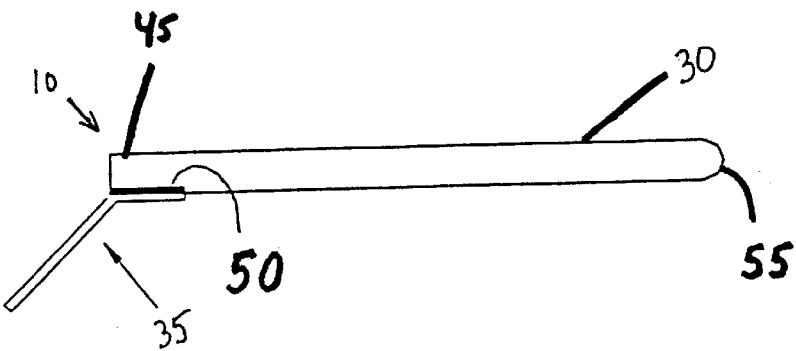
Fig. 1  Side View of Removable Protective Cannula
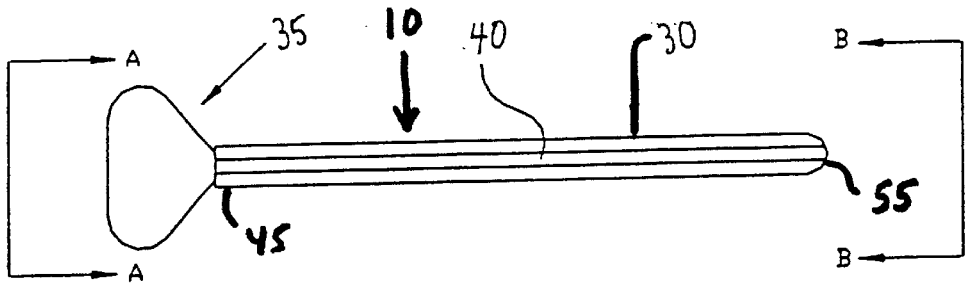
Fig 2  Top View of Removable Protective Cannula
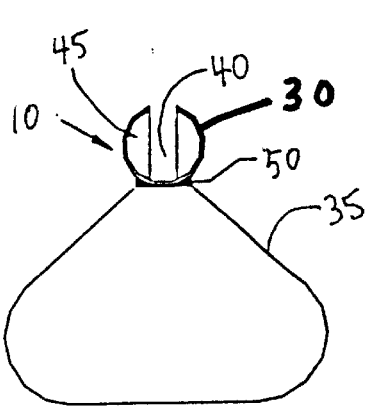
View A-A
Fig. 3
Rear End View
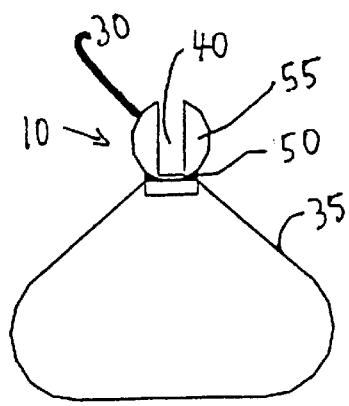
View B-B
Fig. 4
Front End View

US 6,663,605 B2

REMOVABLE PROTECTIVE CANNULA FOR USE IN SURGERY

REFERENCE TO EARLIER APPLICATION

This application claims the benefit of pending prior U.S. Provisional Patent Application Serial No. 60/168,591, filed Dec. 2, 1999, by Kwan-Ho Chan, entitled Removable Protective Cannula For Use In Surgery, which pending prior patent application is hereby incorporated herein by reference.

FIELD OF THE INVENTION

This invention relates to surgical apparatus and procedures in general, and more particularly to a removable cannula useful during arthroscopic or laparoscopic surgery for protecting other apparatus or tissue from damage during insertion of sharp instruments into a patient's body or joint cavity.

BACKGROUND OF THE INVENTION

There are at least two reasons for the need for a novel removable protective cannula to protect other apparatus or tissue from damage during insertion of sharp instruments into a patient's body or joint cavity.

Firstly, cylindrical cannulas, usually made of plastic and sometimes made of metal, are inserted through puncture sites into body or joint cavities. These portal cannulas allow for easy insertion and withdrawal of instruments into and out of the joint or body cavity. There is usually a rubber diaphragm or valve in the proximal part of the cannula to prevent egression of fluid or gas out of the cavity. During laparoscopic or arthroscopic surgery, oftentimes sharp instruments such as suture passers or knives are inserted into the joint or body cavity through the portal cannulas. The sharp distal end of the instrument can cause damage to the diaphragm. Thus, there is a need for a protective apparatus to prevent damage to the rubber diaphragm or valve of the portal cannula during insertion of sharp instruments through the portal cannulas.

Secondly, the maneuverability of instruments inserted through portal cannulas can be restricted due to the bulkiness of the portal cannula itself. This restriction of the maneuverability of surgical instruments can be particularly severe if portal cannulas are clustered close together. Therefore, some surgeons prefer to insert surgical instruments into the body cavity without the use of a portal cannula. However, inserting a sharp instrument through a previous puncture site may inadvertently create new insertion tracks and run the risk of damage to body structures such as nerves or blood vessels. Therefore, there is a need for a protective cannula that protects the surrounding soft tissue during insertion of the sharp instrument, with the protective cannula being removable after the sharp instrument is inserted into the cavity.

SUMMARY OF THE INVENTION

A removable protective cannula is disclosed for use in surgery to prevent damage to a portal cannula or tissue during insertion of a sharp instrument. The removable protective cannula preferably comprises a cylindrical tube, a handle attached at the proximal end of the cylindrical tube, and a slot extending along the length of the cylindrical tube.

In one embodiment of the invention, the width of the slot occupies less than half the circumference of the cylindrical tube.

In another embodiment of the invention, the cylindrical tube has a rounded distal end.

In still another embodiment of the invention, the slot extends substantially the whole diameter of the rounded distal end.

In still yet another embodiment of the invention, the slot is diametrically opposed to the handle.

BRIEF DESCRIPTION OF THE DRAWINGS

The invention will now be described with reference to the accompanying drawings wherein:

FIG. 1 is a side view of a removable protective cannula;

FIG. 2 is a top view of the protective cannula of FIG. 1;

FIG. 3 is an end view of the proximal end of the protective cannula of FIG. 2;

FIG. 4 is an end view of the distal end of the protective cannula of FIG. 2;

DETAILED DESCRIPTION OF THE PREFERRED EMBODIMENTS

Figure 5A:
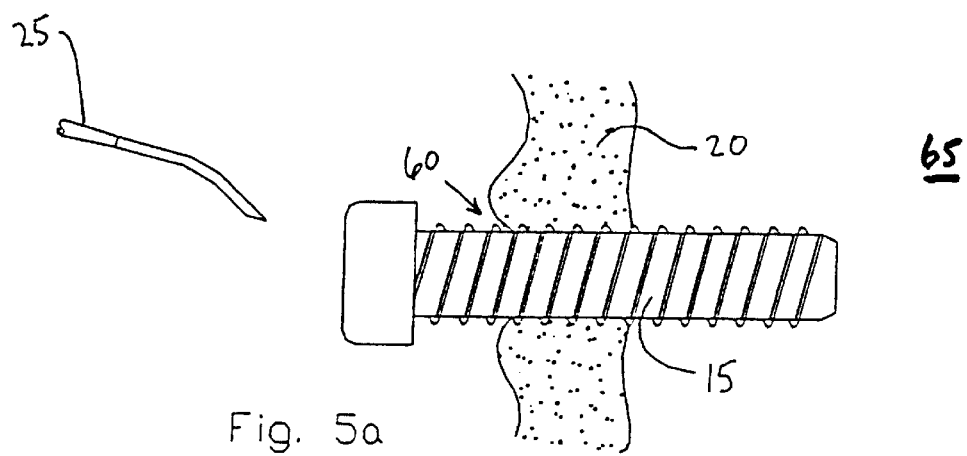
FIGS. 5a–5e are schematic representations illustrating the use of a removable protective cannula for insertion of a sharp instrument through the diaphragm of a portal cannula.

A removable protective cannula 10, as shown in FIGS. 1–4, 5b–5e, and 6b–6e, is disclosed for use in surgery. Removable protective cannula 10 prevents damage to a portal cannula 15, as shown in FIGS. 5a–5e, or to tissue 20, as shown in FIGS. 5a–5e and 6a–6e, during insertion of a sharp instrument, such as a suture passer 25 (FIGS. 5a–5e and 6a–6e).

As shown in FIGS. 1–4, protective cannula 10 includes a cylindrical tube 30, a handle 35 attached to the proximal end of the cylindrical tube 30, and a slot 40 extending along the length of cylindrical tube 30.

Looking now at FIG. 1, handle 35 is attached to a proximal end 45 of protective cannula 10 by a weld 50. A distal end 55 of cylindrical tube 30 is preferably closed off (except for the presence of slot 40 extending therethrough) and rounded for easy insertion through a rubber diaphragm (not shown) of portal cannula 15 and/or tissue 20.

Now looking at FIG. 2, slot 40 preferably extends the entire length of cylindrical tube 30.

Referring to FIGS. 3 and 4, the width of slot 40 preferably occupies less than half the circumference of cylindrical tube 30. Additionally, the depth of slot 40 preferably extends substantially the entire diameter of rounded distal end 55. Also, slot 40 is preferably diametrically opposed to handle 35.

Referring now to FIGS. 5a–5e, a method is shown for using removable protective cannula 10 with suture passer 25 and portal cannula 15 for insertion through a puncture site 60 in tissue 20 into a body or joint cavity 65.

As seen in FIG. 5a, portal cannula 15 is first positioned in tissue 20.

Figure 5B:
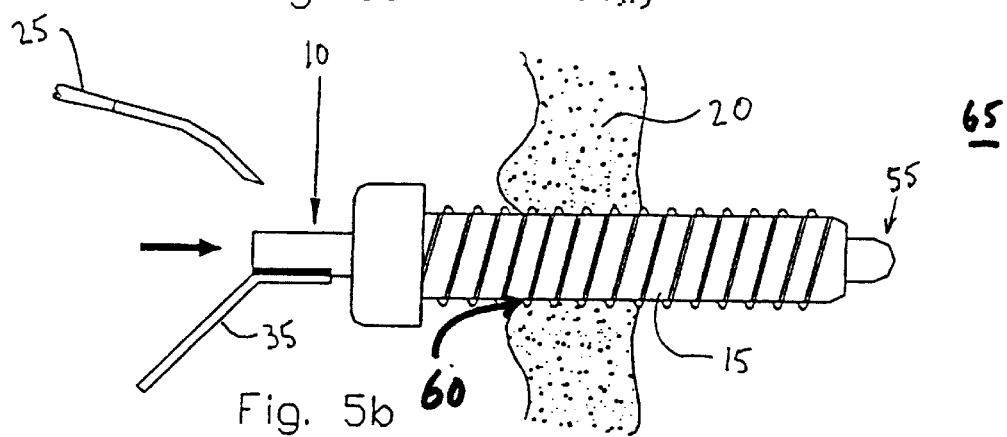

Now looking at FIG. 5b, removable protective cannula 10 is shown inserted through portal cannula 15. Removable protective cannula 10 keeps the leaves of the rubber diaphragm (not shown) inside portal cannula 15 apart during the surgical procedure.

Figure 5C:
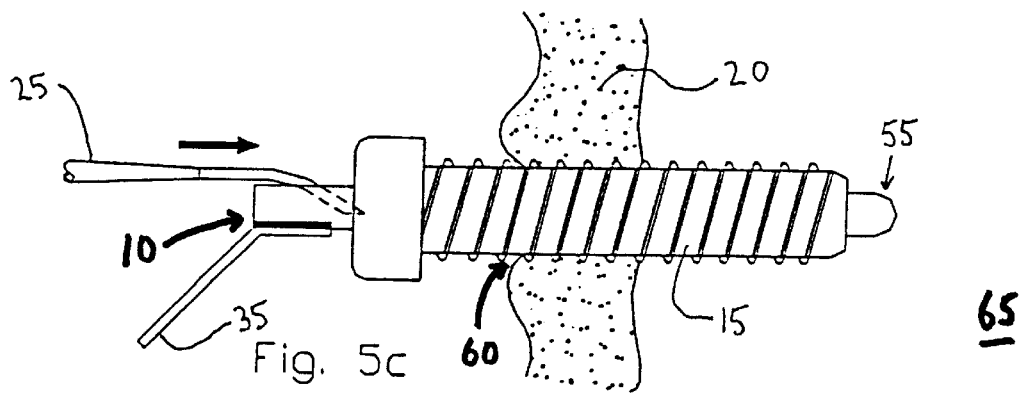
Figure 5D:
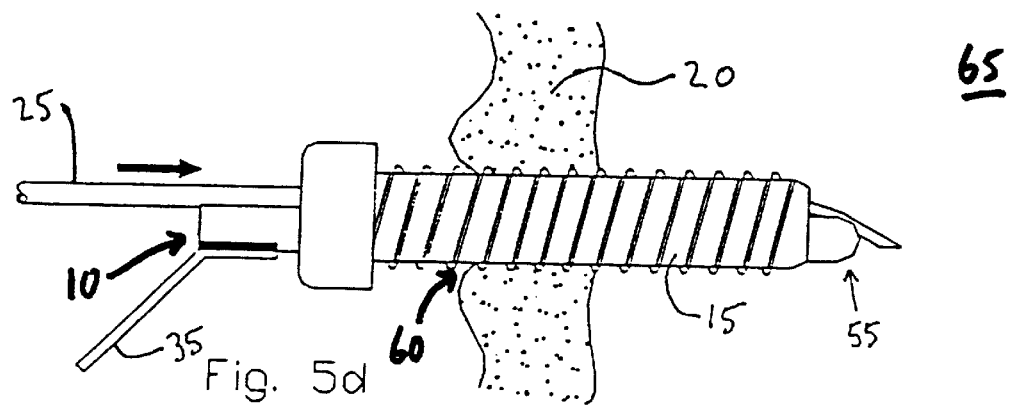
Figure 5E:
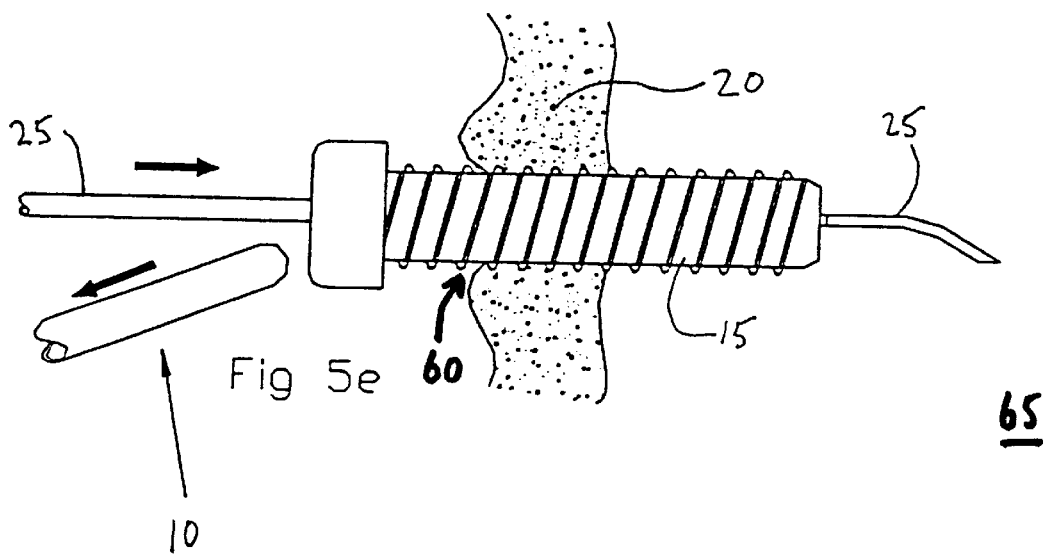

Next, as seen in FIG. 5c, the sharp tip of suture passer 25 is inserted into slot 40 of removable protective cannula 10 before forward advancement of suture passer 25. This prevents damage to the diaphragm of portal cannula 15 when the sharp tip of suture passer 25 is advanced forward. Then, as seen in FIG. 5d, the sharp tip of suture passer 25 is advanced along slot 40 and beyond distal end 55 of removable protective cannula 10 and into cavity 65.

Removable protective cannula 10 may then be withdrawn from portal cannula 15 (FIG. 5e) and disengaged from suture passer 25. This improves the maneuverability of suture passer 25.

Referring now to FIGS. 6a–6e, a method is shown for using removable protective cannula 10 with suture passer 25 for insertion through puncture site 60 in tissue 20 into cavity 65.

Figure 6A:
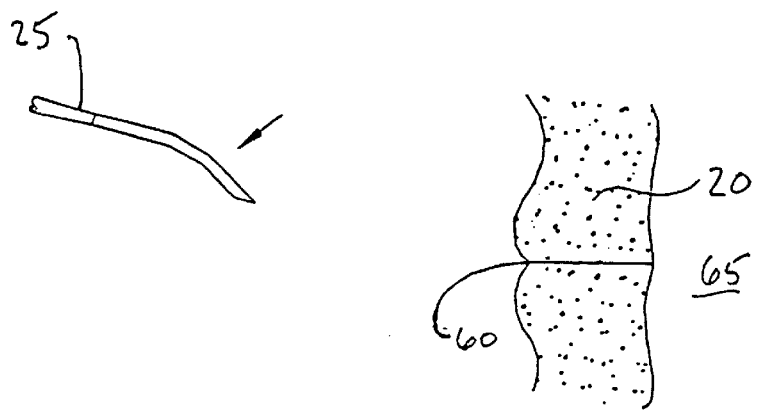
FIGS. 6a–6e are schematic representations of a removable protective cannula used in combination with a suture passer.
Figure 6B:
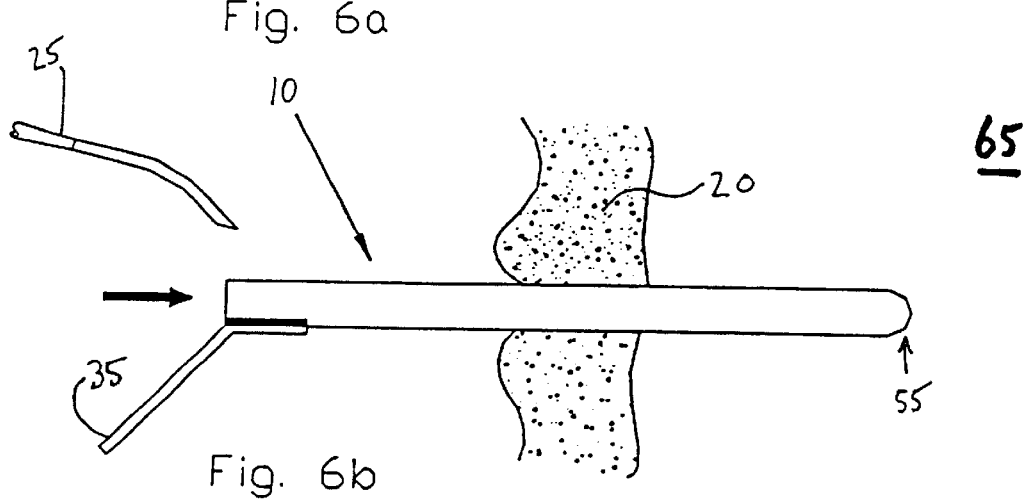
Figure 6C:
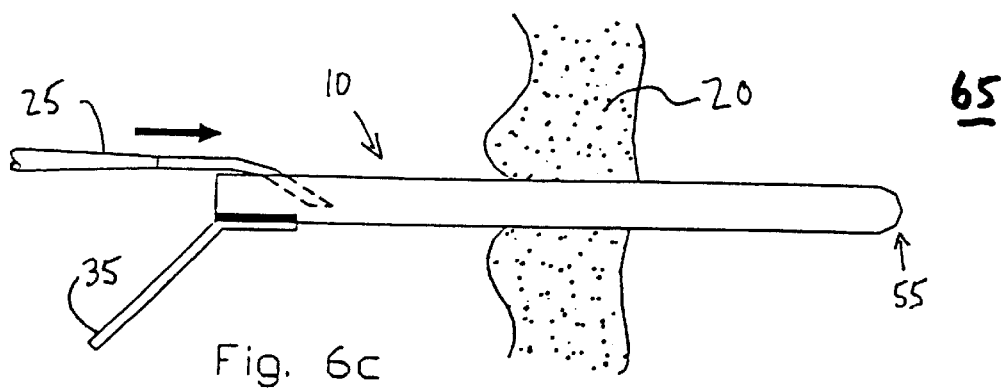
Figure 6D:
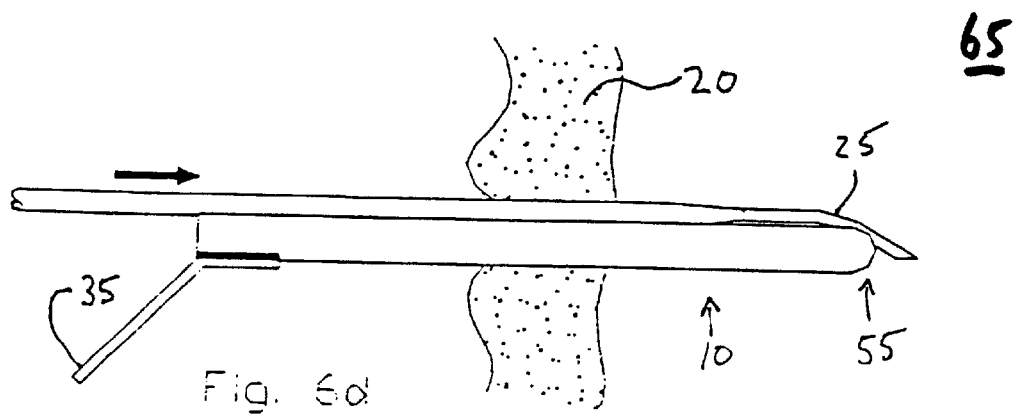
Figure 6E:
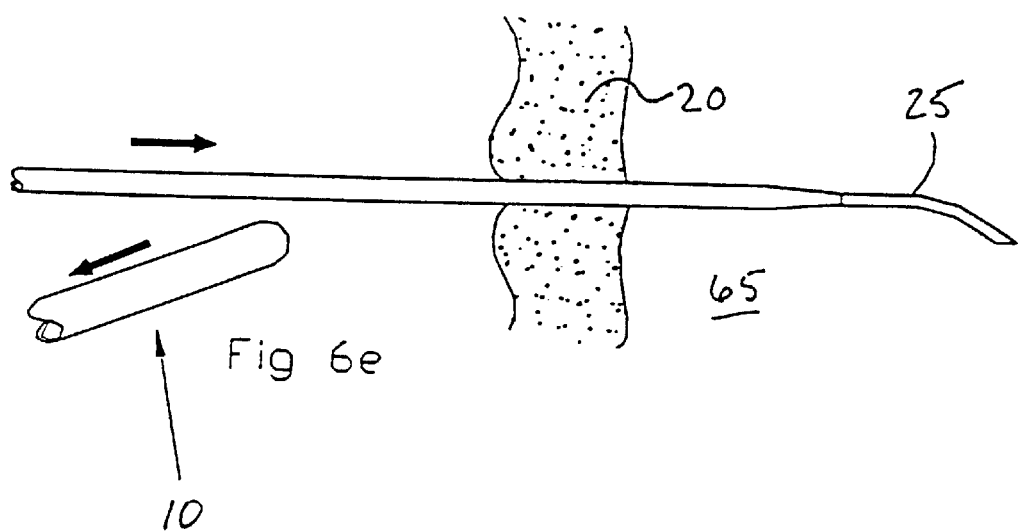

Now looking at FIG. 6b, removable protective cannula 10 is first shown inserted through tissue 20. Next, the sharp tip of suture passer 25 is inserted into slot 40 of removable protective cannula 10 before forward advancement of suture passer 25 (FIG. 6c). This prevents damage to tissue 20 and the creation of new tracks when the sharp tip of suture passer 25 is advanced forward. The sharp tip of suture passer 25 is advanced down slot 40 and beyond distal end of removable protective cannula 10 and into cavity 65 (FIG. 6d). Removable protective cannula 10 is next withdrawn from puncture site 60 and disengaged from suture passer 25 (FIG. 6e). The suture passer is thus positioned inside cavity 65 without any intervening cannula. This improves the maneuverability of suture passer 25.

If desired, the protective cannula's cylindrical tube 30 can be replaced by a substantially solid shaft in which slot 40 extends.

It should be understood that the specific embodiments shown herein are presented by way of illustration and not limitation, and that various changes and modifications may be made by one skilled in the art without departing from the scope and spirit of the invention.

What is claimed is:

1. A protective cannula for use in surgery to prevent damage to a portal cannula or tissue during insertion of a sharp instrument therethrough comprising:
    a shaft;
    a handle attached to the proximal end of said shaft; and
    a slot extending along substantially the entire length of said shaft.

2. A protective cannula according to claim 1 wherein said shaft comprises a cylindrical tube.

3. A protective cannula according to claim 2 wherein said cylindrical tube includes a distal end wall.

4. A protective cannula according to claim 1 wherein the width of said slot occupies less than half the circumference of said shaft.

5. A protective cannula according to claim 1 wherein said shaft has a rounded distal end.

6. A protective cannula according to claim 1 wherein said slot extends the entire diameter of said rounded distal end.

7. A protective cannula according to claim 1 wherein said slot is diametrically opposed to said handle.

8. A method for passing a sharp instrument through an object without damaging the object, said method comprising the steps of:
    providing a protective cannula comprising a shaft, a handle attached to the proximal end of the shaft, and a slot extending along the length of the shaft;
    passing the protective cannula through the object so that the distal end of the cannula is positioned on one side of the object and the proximal end of the cannula is positioned on the other side of the object; and
    passing the sharp instrument down the slot in the cannula.

9. A protective cannula for use in surgery to prevent damage to a portal cannula or tissue during insertion of a sharp instrument therethrough comprising:
    a shaft;
    a handle attached to the proximal end of said shaft; and
    a slot extending along the length of said shaft;
    wherein said shaft has a rounded distal end.

10. A protective cannula for use in surgery to prevent damage to a portal cannula or tissue during insertion of a sharp instrument therethrough comprising:
    a shaft;
    a handle attached to the proximal end of said shaft; and
    a slot extending along the length of said shaft;
    wherein said slot is diametrically opposed to said handle.

* * * * *